United States Patent
Atallah et al.

(10) Patent No.: US 10,064,566 B2
(45) Date of Patent: Sep. 4, 2018

(54) ELECTROCARDIOGRAPHY MONITORING SYSTEM AND METHOD

(71) Applicant: KONINKLIJKE PHILIPS N.V., Eindhoven (NL)

(72) Inventors: Louis Nicolas Atallah, Eindhoven (NL); Mohammed Meftah, Tilburg (NL); Martijn Schellekens, Eindhoven (NL); Aline Anne Marie Serteyn, Eindhoven (NL); Rik Vullings, Venray (NL); Jan Bergmans, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/038,289

(22) PCT Filed: Nov. 24, 2014

(86) PCT No.: PCT/IB2014/066281
§ 371 (c)(1),
(2) Date: May 20, 2016

(87) PCT Pub. No.: WO2015/075692
PCT Pub. Date: May 28, 2015

(65) Prior Publication Data
US 2016/0287129 A1    Oct. 6, 2016

Related U.S. Application Data

(60) Provisional application No. 61/908,193, filed on Nov. 25, 2013.

(51) Int. Cl.
*A61B 5/0408* (2006.01)
*A61B 5/00* (2006.01)
(Continued)

(52) U.S. Cl.
CPC ...... *A61B 5/04085* (2013.01); *A61B 5/04011* (2013.01); *A61B 5/04017* (2013.01);
(Continued)

(58) Field of Classification Search
CPC ............ A61B 5/04085; A61B 5/04011; A61B 5/04017; A61B 5/04284; A61B 5/04325;
(Continued)

(56) References Cited

U.S. PATENT DOCUMENTS

| | | | |
|---|---|---|---|
| 3,500,823 | A | 3/1970 | Richardson |
| 7,885,700 | B2 | 2/2011 | Clark |

(Continued)

FOREIGN PATENT DOCUMENTS

| | | |
|---|---|---|
| WO | 2007/060609 | 5/2007 |
| WO | 2009/013245 | 1/2009 |
| WO | 2013/072839 | 5/2013 |

OTHER PUBLICATIONS

Saadane, "Detection of the abdominal fetal electrocardiogram", Dec. 1, 2005.

(Continued)

*Primary Examiner* — Carl H Layno
*Assistant Examiner* — Erin M Piateski

(57) ABSTRACT

Systems and methods for electrocardiography monitoring use multiple capacitive sensors in order to determine reliable measurements of electrophysiological information of a patient. Relative coupling strength and/or reliability is used to select dynamically which sensors to use in order to determine, in particular, an electrocardiogram of the patient.

17 Claims, 5 Drawing Sheets

(51) Int. Cl.
| | |
|---|---|
| A61G 11/00 | (2006.01) |
| A61B 5/04 | (2006.01) |
| A61B 5/0428 | (2006.01) |
| A61B 5/0432 | (2006.01) |
| A61B 5/0452 | (2006.01) |
| A61B 5/0456 | (2006.01) |
| A61B 5/0402 | (2006.01) |
| A61B 5/0424 | (2006.01) |

(52) U.S. Cl.
CPC ........ *A61B 5/0456* (2013.01); *A61B 5/04284* (2013.01); *A61B 5/04325* (2013.01); *A61B 5/04525* (2013.01); *A61B 5/6892* (2013.01); *A61B 5/7214* (2013.01); *A61B 5/7221* (2013.01); *A61G 11/00* (2013.01); *A61B 5/0424* (2013.01); *A61B 5/04028* (2013.01); *A61B 2503/04* (2013.01); *A61B 2503/045* (2013.01); *A61B 2503/40* (2013.01); *A61B 2562/0214* (2013.01)

(58) Field of Classification Search
CPC . A61B 5/04525; A61B 5/0456; A61B 5/6892; A61B 5/7214; A61B 5/7221; A61B 5/04028; A61B 5/0424; A61B 2503/04; A61B 2503/045; A61B 2503/40; A61G 11/00
USPC ....... 600/372, 547, 384, 511, 481, 393, 509, 600/512; 607/8
See application file for complete search history.

(56) References Cited

U.S. PATENT DOCUMENTS

| | | |
|---|---|---|
| 8,332,021 B2 | 12/2012 | Vullings |
| 8,369,936 B2 | 2/2013 | Farringdon |
| 2006/0041196 A1 | 2/2006 | Matthews et al. |
| 2007/0038257 A1* | 2/2007 | Gray .................... A61B 5/0424 607/8 |
| 2007/0276270 A1* | 11/2007 | Tran .................... A61B 5/0022 600/508 |
| 2008/0208063 A1* | 8/2008 | Brauers .............. A61B 5/04085 600/481 |
| 2010/0185108 A1* | 7/2010 | Vullings ............ A61B 5/04011 600/511 |
| 2011/0125002 A1 | 5/2011 | Ershov et al. |
| 2011/0137200 A1 | 6/2011 | Yin |
| 2012/0116198 A1 | 5/2012 | Veen |

OTHER PUBLICATIONS

Evans, et al., "Development of the Epidermis in the Newborn", Biol. Neonate 49:74-80; 1986.
Lim, et al., "The ECG Measurement in the Bathtub Using the Insulated Electrodes", Proceedings of the 26th Annual International Conference of the IEEE EMBS, Sep. 1-5, 2004.
Kim, et al., "The Electrically Non-contacting ECG Measurement on the Toilet Seat Using the Capacitively-coupled Insulated Electrodes", Proceedings of the 26th Annual International Conference of the IEEE EMBS, Sep. 1-5, 2004.
Leonhardt, et al., "Non-Contact ECG Monitoring for Automotive Application", 2008 IEEE.
Kato, et al., "An Application of Capacitive Electrode for Detecting Electrocardiogram of Neonates and Infants", 2006 IEEE.
Weil, et al., "First clinical evaluation of a novel capacitive ECG system in patients with acute myocardial infarction", Clin Res Cardiol (2012) 101:165-174.
Oehler, et al., "A multichannel portable ECG system with capacitive sensors", Physiol. Meas. 29 (2008) 783-793.
Eilebrecht, et al., "Automatic Parameter Extraction from Capacitive ECG Measurements", Cardiovascular Engineering and Technology, vol. 3, No. 3, Sep. 2012.
Feldman, et al., "Comparison of Skin-to-Skin (Kangaroo) and Traditional Care: Parenting Outcomes and Preterm Infant Development", Pediatrics, Aug. 2002.
McCain, et al., "Heart Rate Variability Responses of a Preterm Infant to Kangaroo Care", JOGNN 2005.
Wartzek, et al., "Automatic Electrode Selection in Unobtrusive Capacitive ECG Measurements", 2012 IEEE.
Vullings, et al., "Bayesian Approach to Patient-Tailored Vectorcardiography", IEEE Transactions on Biomedical Engineering, vol. 57, No. 3, Mar. 2010.
Vullings, et al., "A robust physiology-based source separation method for QRS detection in low amplitude fetal ECG recordings", Physiol. Meas. 31 (2010) 935-951.
Rooijakkers, et al., "Low-complexity R-peak detection for ambulatory fetal monitoring". Physiol. Meas. 33 (2012) 1135-1150.
Vullings, et al., "An Adaptive Kalman Filter for ECG Signal Enhancement", IEEE Transactions on Biomedical Engineering, vol. 58, No. 4, Apr. 2010.
Vullings, et al., "Non-invasive fetal electrocardiogram: analysis and interpretation", 2010.

* cited by examiner

ELECTROCARDIOGRAPHY MONITORING SYSTEM AND METHOD

CROSS REFERENCE TO RELATED APPLICATIONS

This application is the U.S. National Phase application under 36 U.S.C. § 371 of International Application No. PCT/IB2014/066281, filed Nov. 24, 2014, published as WO 2015/075692 on May 28, 2015, which claims the benefit of U.S. Provisional Patent Application No. 61/908,193 filed Nov. 25, 2013. These applications are hereby incorporated by reference herein.

BACKGROUND

1. Field

The present disclosure pertains to systems and methods for electrocardiography (ECG) monitoring.

2. Description of the Related Art

Monitoring heart activity is known to be widely used. Traditionally, electrocardiography (ECG) monitoring produces important information for medical professionals. Invasive techniques, including, but not limited to, adhesive electrodes and tape can be uncomfortable for some subjects, in particular those having sensitive, new, or thin skin. Non-invasive techniques, for example using capacitive electrodes, sometimes suffer from motion artifacts.

SUMMARY

Accordingly, one or more embodiments provide a system configured for electrocardiography (ECG) monitoring of a subject. The system includes multiple capacitive sensors and one or more processors. The multiple capacitive sensors are configured to generate output signals conveying electrophysiological information of the subject. Individual ones of the capacitive sensors are further configured to emit carrier signals. The generated output signals include a representation of the) emitted carrier signals. The one or more processors are configured to execute computer program modules. The computer program modules include a coupling module, a selection module, and a reconstruction module. The coupling module is configured to determine coupling levels for individual ones of the capacitive sensors based on the output signals. The selection module is configured to select one or more capacitive sensors based on the determined coupling levels, among other factors The reconstruction module is configured to determine an electrocardiogram (ECG) signal based on the generated output signals of the selected one or more capacitive sensors.

It is yet another aspect of one or more embodiments to provide a method of providing electrocardiography (ECG) monitoring of a subject. The method includes emitting, by multiple capacitive sensors, carrier signals; generating, by the multiple capacitive sensors, output signals conveying electrophysiological information of the subject, wherein the output signals include a representation of the emitted carrier signals; determining coupling levels for individual ones of the capacitive sensors based on the generated output signals; selecting one or more capacitive sensors based on the determined coupling levels, among other factors; and determining an electrocardiogram (ECG) signal based on the generated output signals of the selected one or more capacitive sensors.

It is yet another aspect of one or more embodiments to provide a system configured to provide electrocardiography (ECG) monitoring of a subject. The system includes means for emitting carrier signals including multiple elements configured to emit carrier signals; means for generating output signals conveying electrophysiological information of the subject, wherein the output signals include a representation of the emitted carrier signals; means for determining coupling levels for the means for emitting carrier signals based on the generated output signals; means for selecting one or more elements of the means for emitting carrier signals based on the determined coupling levels, among other factors; and means for determining an electrocardiogram signal based on the generated output signals of the selected elements selected by the means for selecting.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
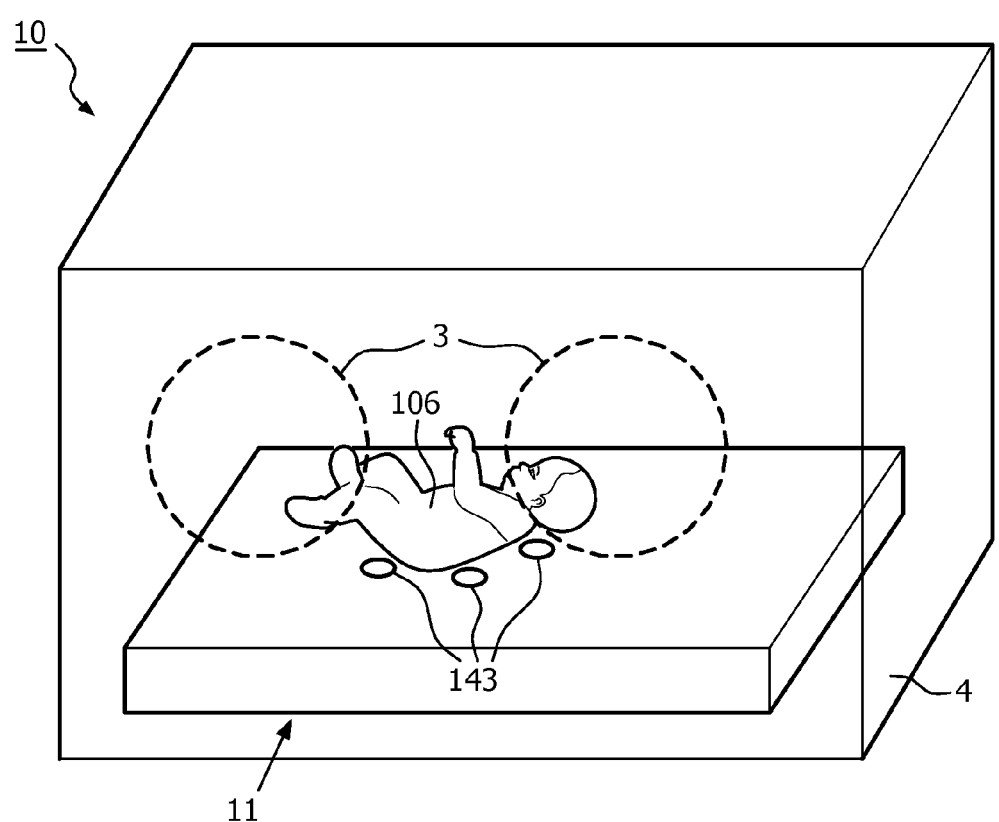
FIG. 1 illustrates a system for monitoring of a subject, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 3:
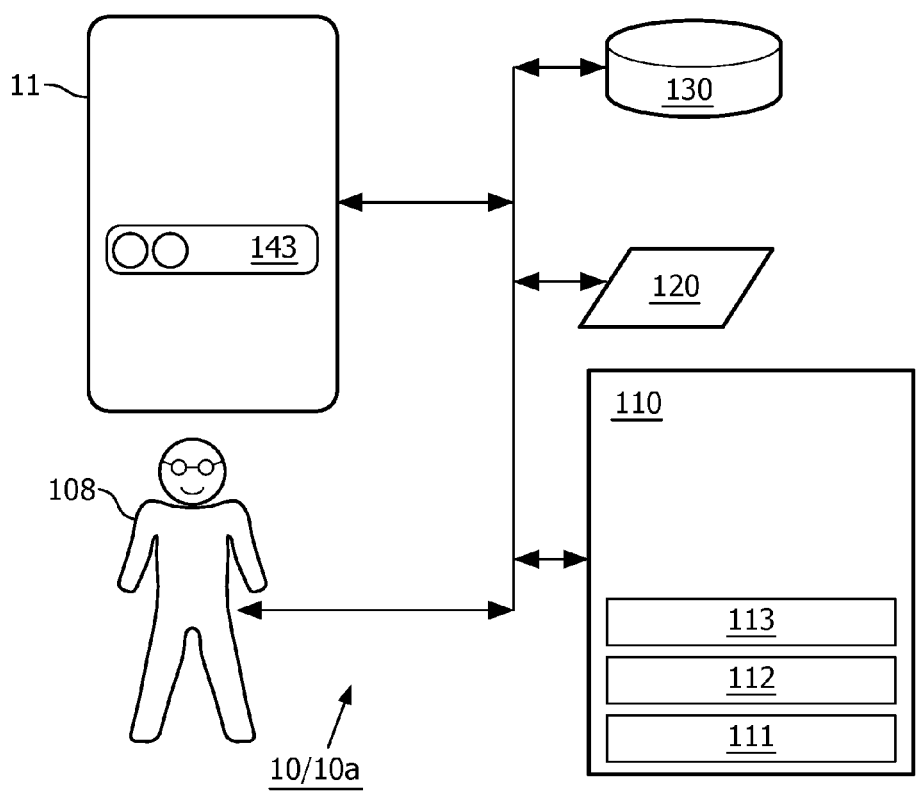
FIG. 3 schematically illustrates a system for monitoring of a subject, in accordance with one or more embodiments.

FIG. 1 illustrates a system 10 for (non-invasive) monitoring of a subject 106. System 10 may interchangeably be referred to as "monitoring system 10". System 10 may include one or more of a body of engagement 11, an incubator 4 having access apertures 3, multiple capacitive sensors 143, and/or other components (including components illustrated in other figures as being included in system 10). Body of engagement 11 may interchangeably be referred to as "structure of engagement," "structure," "support-structure of engagement," or "support-structure." By way of non-limiting example, FIG. 3 schematically illustrates system 10a, which may include all components and features attributed to system 10 as elsewhere described herein, and which may further include, as depicted in FIG. 3, one or more of an electronic storage 130, a user interface 120, one or more processors 110, one or more computer program modules, and/or other components. Referring to FIG. 3, the computer program modules may include one or more of a coupling module 111, a selection module 112, a reconstruction module 113, and/or other modules. Also illustrated in FIG. 3 is a user 108 of system 10 such as, by way of non-limiting example, a care-giver, a therapy-decision-maker, and/or a medical professional.

Non-invasive, unobtrusive, and/or motion-tolerant determination of heart activity of a subject, including electrocardiography (ECG), and in particular for neonates and/or infants, may contribute to the availability of medically and/or diagnostically relevant information without causing the damage, stress, pain, and/or discomfort associated with invasive techniques. The techniques described in this disclosure may be applied to both humans and animals. Changes over time in such monitored parameters may be particularly relevant. As used herein, the term "non-invasive" may refer to the absence of adhesives to keep sensors in place and/or the absence of physical equipment penetrating or adhering to the skin or being inserted in any manner into the subject. Adhesive sensors may damage the (very thin) skin and cause stress, discomfort, and/or pain when used. As used herein, the term "motion-tolerant" may refer to the ability to obtain reliable measurements in the presence of limited motion by subject 106. Wriggling, movement of arms, legs, and head, rolling from side-to-side, transitions between different body positions, movements caused by the subject being agitated or unwell, and/or similar movements may be interpreted as limited motion. In some embodiments, in situ and/or in place handling of subject 106, including but not limited to feeding, diaper changes, test-taking, and/or other actions commonly performed when treating or caring for neonates and/or infants may be interpreted as limited motion as long as subject 106 remains within a predetermined distance of capacitive sensors 143. This predetermined distance may be relative to a particular individual capacitive sensor, to all capacitive sensors used in a particular embodiment, to an average distance from multiple capacitive sensors, and/or otherwise specified for a particular embodiment. Measurements during periods when subject 106 is more than the predetermined distance from capacitive sensors 143 may not be interpreted as limited motion, regardless of the actual movement of subject 106. Medical conditions and/or issues mentioned in this disclosure are intended to be exemplary and without limitation.

Figure 2A:
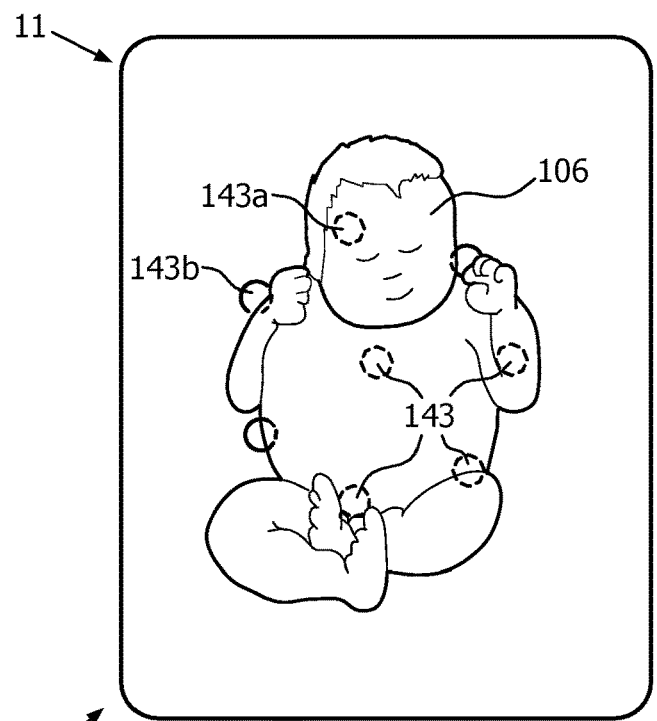
FIGS. 2A-2B illustrate a system in accordance with one or more embodiments.
Figure 2B:
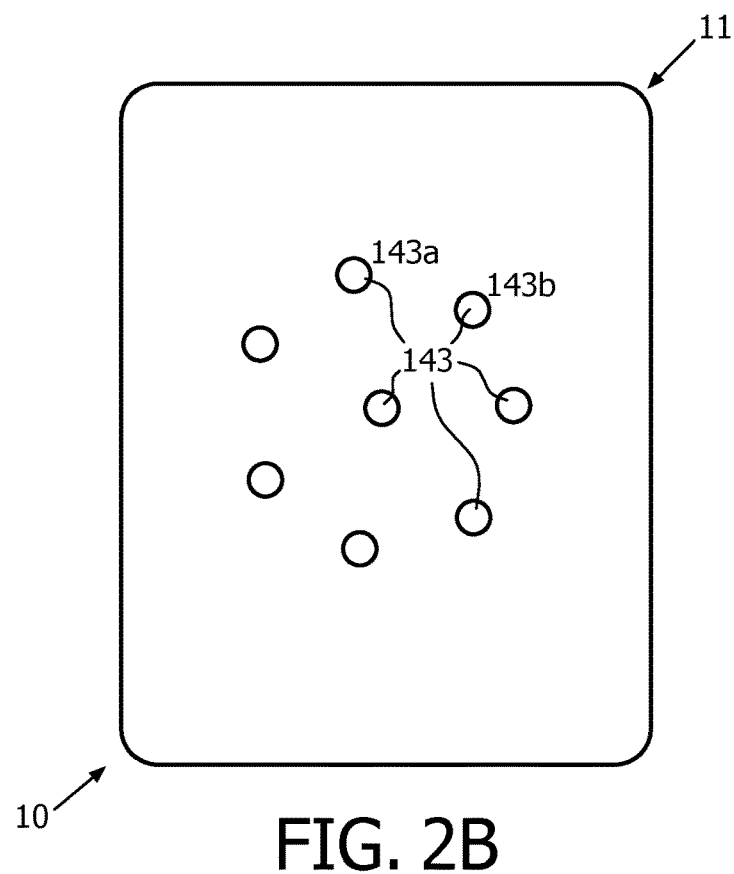

Referring to FIG. 1, body of engagement 11 is configured to engage with a subject 106, e.g. a neonate and/or infant. In some embodiments, body of engagement 11 may be implemented as a (subject) support structure configured to support subject 106 thereon. A subject support structure may be a mattress, a bed, a pad, a blanket, a wrap, a pillow, an incubator, and/or other structure suitable to engage and/or support subject 106. In some embodiments, body of engagement 11 may be an article of clothing configured to be worn by and/or wrapped around subject 106. Body of engagement 11 may be configured to carry one or more sensors, e.g. one or more capacitive sensors 143. By way of illustration, FIGS. 2A and 2B illustrates a top-view of system 10, including body of engagement 11 and multiple capacitive sensors 143. In FIG. 2A, subject 106 is placed on top of body of engagement 11, thus obscuring one or more capacitive sensors 143 from being directly visible, as indicated by dotted lines in FIG. 2A. FIG. 2B illustrates the same system 10 and the same body of engagement as depicted in FIG. 2A, but without subject 106 obscuring part of the view. The number of capacitive sensors 143 as depicted is merely exemplary, and not intended to be limiting in any way. The pattern and/or arrangement of capacitive sensors 143 as depicted in FIG. 2B, e.g. resembling flow petals, is merely exemplary, and not intended to be limiting in any way.

As used herein, a generic reference to a capacitive sensor or a reference to multiple capacitive sensors may use the terms "capacitive sensor 143," or "capacitive sensor(s) 143," or variations thereof using the reference numeral "143," whereas a specific individual capacitive sensor may be referred to by appending a character to that reference numeral, e.g. "capacitive sensor 143a", or "capacitive sensor 143b," depicted in FIG. 2B. The disclosure is not limited to the number or position of any sensors depicted in any of the figures. As used herein, the term "measure" refers to any combination of measuring, estimating, and/or approximating based on output generated by one or more sensors. As used herein, the term "measurement" refers to any combination of one or more measurements, estimations, determinations, inferences, and/or approximations based on output generated by one or more sensors.

Capacitive sensor(s) 143 may be configured to generate output signals conveying one or more types of information, collectively referred to as sensed information. In particular, capacitive sensor(s) 143 may be configured to generate output signals conveying electrophysiological information of subject 106 and/or output signals conveying information related in a predictable manner (e.g. through a mathematical relationship) to electrophysiological parameters of subject 106, which may collectively be referred to as electrophysiological information. The sensed information may include electrophysiological information. Capacitive sensors effectively may form a capacitor in which the skin of subject 106 acts as one of the capacitor plates and an electrode of the capacitive sensor acts as the other capacitive plate of the capacitor. Capacitive sensor(s) 143 may be supported and/or carried by body of engagement 11.

In some embodiments, capacitive sensor(s) 143 may be configured to generate output signals conveying electrical and/or other coupling information between two objects (e.g. the sensor itself and subject 106). In some embodiments, sensed information may include coupling information and/or electrophysiological information.

In some embodiments, coupling information may be conveyed by the intensity, strength, magnitude, spectral information, phase shift, and/or level of a signal generated by capacitive sensor(s) 143. For example, referring to FIG. 2A, in some embodiments, an individual capacitive sensor 143a may emit a signal (e.g. an electromagnetic signal) having one or more known characteristics (including but not limited to a known frequency, phase, shape, magnitude, and/or other characteristic of an electromagnetic signal). Such an emitted signal may be referred to as a carrier signal. Coupling information for individual capacitive sensor 143*a* may be determined by and/or based on how well the emitted signal is received by individual capacitive sensor 143*a*. The sensed information may include at least a component that corresponds to and/or represents a carrier signal, and this component may be used to determine coupling information and/or as basis for such a determination. In some embodiments, the sensed information may include a modulated carrier signal (and/or modulated version of a carrier signal) that is a version of the carrier signal that has been modulated and/or influenced by the capacitive coupling between a capacitive sensor 143 and (the skin of) subject 106.

As used herein, the term "capacitive sensor" is not intended to be limited to structures for receiving and/or sensing signals, but may include structures for transmitting, emitting, transferring, broadcasting, generating, and/or creating signals. Such "capacitive sensors" may interchangeably be referred to as "capacitive transceivers," and derivatives thereof. In case of good and/or strong coupling between capacitive sensor 143*a* and subject 106, the received signal (e.g. the portion or component of the sensed information that corresponds to the carrier signal) may have, e.g., a greater magnitude than compared to a case of poor and/or weak coupling between the capacitive sensor 143*a* and subject 106.

In some embodiments, the portion or component of the sensed information that corresponds to the emitted carrier signal (and/or is a representation of the emitted carrier signal) may be distinguished from the portion or component of the sensed information conveying electrophysiological information by virtue of having distinguishing (electromagnetic) characteristics, including but not limited to frequency, phase, shape, magnitude, and/or other characteristic of an electromagnetic signal. For example, the electrophysiological information may be (biologically) limited to a (predetermined) range of frequencies and/or other characteristics. Capacitive sensors 143 may be configured to emit a carrier signal. In some embodiments, the emitted carrier signal may have a characteristic outside of the limited range. For example, the carrier signals emitted by capacitive sensors 143 may have one or more higher frequencies (e.g. about 1 kHz, about 10 kHz, about 100 kHz, about 1 MHz, and/or other suitable frequencies) than the range of frequencies of the electrophysiological information (e.g. below 1 kHz, and/or below/above the suitable frequency chosen and/or selected for capacitive sensors 143). System 10 may distinguish electrophysiological information from coupling information in the sensed information by filtering and/or using signal-processing techniques suitable for the chosen and/or selected distinguishing feature(s) described herein. In addition to using the carrier signals to perform channel selection, as explained elsewhere in this disclosure, the carrier signals may be used to reconstruct the electrocardiogram (ECG) signal.

In some embodiments, system 10 may include 3, 4, 5, 6, 7, 8, or more capacitive sensors 143. By way of illustration, FIG. 2B illustrates an exemplary embodiment of system 10 that includes 8 capacitive sensors 143. Systems using one or two capacitive sensors 143 may not be motion-tolerant, and/or may not be able to determine reliable measurements in multiple different body positions, including but not limited to supine, prone, and/or on the side.

Sensors in this disclosure may be configured to generate output signals in an ongoing manner, e.g. throughout the day. This may include generating signals intermittently, periodically (e.g. at a sampling rate), continuously, continually, at varying intervals, and/or in other ways that are ongoing during at least a portion of period of a day, week, month, or other duration. The sampling rate may be about 0.001 second, 0.01 second, 0.1 second, 1 second, about 10 seconds, about 1 minute, and/or other sampling rates. It is noted that multiple individual sensors may operate using different sampling rates, as appropriate for the particular output signals and/or (frequencies related to particular) parameters derived therefrom. For example, in some embodiments, the generated output signals may be considered as a vector of output signals, such that a vector includes multiple samples of information conveyed related to one or more parameters of subject 106. Different parameters may be related to different vectors. A particular parameter determined in an ongoing manner from a vector of output signals may be considered as a vector of that particular parameter.

Referring to system 10 of FIG. 3 (and/or system 10*a*, as used interchangeably in reference to FIG. 3), system 10 may include electronic storage 130 comprising electronic storage media that electronically stores information. The electronic storage media of electronic storage 130 includes one or both of system storage that is provided integrally (i.e., substantially non-removable) with system 10 and/or removable storage that is connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 stores software algorithms, information determined by processor 110, information received via user interface 120, and/or other information that enables system 10 to function properly. For example, electronic storage 130 may record or store (a set of) one or more parameters derived from output signals measured (e.g. over time) by one or more sensors (as discussed elsewhere herein), and/or other information. Electronic storage 130 may be a separate component within system 10, or electronic storage 130 may be provided integrally with one or more other components of system 10 (e.g., processor 110).

Referring to FIG. 3, system 10 may include user interface 120 configured to provide an interface between system 10 and a user (e.g., user 108, a caregiver, a therapy decision-maker, etc.) through which the user can provide information to and receive information from system 10. This enables data, results, and/or instructions and any other communicable items, collectively referred to as "information," to be communicated between the user and system 10. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may e.g. be provided to user 108 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 may control the radiation source to emit light in a manner that conveys information to, e.g., user 108 related to, e.g., a breaching of a predetermined heart-rate threshold by subject 106.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Referring to FIG. 3, processor 110 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 3 as a single entity, this is for illustrative purposes only. In some embodiments, processor 110 includes a plurality of processing units.

As is shown in FIG. 3, processor 110 is configured to execute one or more computer program modules. The one or more computer program modules include one or more of coupling module 111, selection module 112, reconstruction module 113, and/or other modules. Processor 110 may be configured to execute modules 111-113 by software; hardware; firmware; some combination of software, hardware, and/or firmware; and/or other mechanisms for configuring processing capabilities on processor 110, including programmable hardware.

It should be appreciated that although modules 111-113 are illustrated in FIG. 3 as being co-located within a single processing unit, in implementations in which processor 110 includes multiple processing units, one or more of modules 111-113 may be located remotely from the other modules. The description of the functionality provided by the different modules 111-113 described below is for illustrative purposes, and is not intended to be limiting, as any of modules 111-113 may provide more or less functionality than is described. For example, one or more of modules 111-113 may be eliminated, and some or all of its functionality may be provided by other ones of modules 111-113. Note that processor 110 may be configured to execute one or more additional modules that may perform some or all of the functionality attributed below to one of modules 111-113.

Coupling module 111 of system 10 in FIG. 3 is configured to determine coupling levels for one or more capacitive sensors 143 of system 10. As used herein, the term "coupling level" may refer to coupling strength (e.g. of electrical signals), and/or signal strength (e.g. of electrical signals). In some embodiments, coupling levels may be based on the intensity, amplitude, strength, magnitude, energy content, capacitive levels, spectral information, phase shift and/or other types of levels and/or combinations thereof that may indicate whether (and/or to what extent) the output signal from a capacitive sensor 143 should be deemed reliable. Alternatively, and/or simultaneously, in some embodiments, a coupling level may indicate whether the output signal from a capacitive sensor 143 should be discarded, e.g. in favor of stronger and/or more reliable signals from other capacitive sensors 143. Determinations of coupling levels by coupling module 111 may be based on the entire output signal (e.g. the entire sensed information) or on one or more portions or components thereof (e.g. one or more portions or components that correspond to the coupling information). For example, in some embodiments, the coupling level for a particular capacitive sensor 143a may be based on the magnitude of the portion of the output signal that falls in a particular frequency range, e.g. above 1 kHz. The portion of the output signal falling in the particular frequency range corresponds to the coupling information. In some embodiments, the coupling level may be based on a characteristic of the entire output signal, instead of a portion thereof.

The coupling level for an individual capacitive sensor 143 may change over time, for example between individual measurements taken. Changes in coupling levels over time may, for example, be caused by movement of subject 106. Coupling module 111 may be configured to order, rank, and/or otherwise compare coupling levels of a capacitive sensor 143 to coupling levels from one or more other capacitive sensors 143. Coupling module 111 may be configured to determine coupling levels for some or all capacitive sensors 143 at the same or similar sampling rate such that changing coupling levels may be reevaluated at the same or similar sampling rate to determine whether to use or discard corresponding measurements from associated capacitive sensors 143.

In some embodiments, coupling module 111 may be configured to determine which particular capacitive sensor 143 has the highest and/or strongest coupling level from a set of capacitive sensors 143. This particular capacitive sensor 143 may be referred to as the maximum capacitive sensor. The maximum capacitive sensor may change from one particular capacitive sensor 143a to another particular capacitive sensor 143b, e.g. subsequent to measurements being taken on both capacitive sensors. The coupling level of the maximum capacitive sensor may be referred to as the maximum coupling level. In some embodiments, coupling module 111 may be configured to determine an aggregate coupling level for one or more capacitive sensors 143. For example, the aggregate coupling level may be based on one or more of the average value, mean value, standard deviation, variance, and/or other statistical and/or aggregate function that produces one output values from multiple coupling levels. The coupling levels used to determine the aggregate coupling level may include coupling levels from all available capacitive sensors 143, all available capacitive sensors except the maximum capacitive sensor, all available capacitive sensors 143 that have a coupling level at least high or strong enough to breach a minimum coupling threshold, all available capacitive sensors except the maximum sensor that have a coupling level at least high or strong enough to breach a minimum coupling threshold, and/or other subsets of the capacitive sensors 143 that may be reevaluated subsequent to measurements being taken, e.g. at the sampling rate.

Selection module 112 of system 10 in FIG. 3 is configured to select one or more capacitive sensors 143. Selection module 112 may applied multiple selections in sequence to discard one or more capacitive sensors 143. Output signals from the one or more selected capacitive sensors may be used, e.g. by reconstruction module 113 to determine an electrocardiogram (ECG) signal and/or parameter. Selection by selection module 112 may be based on coupling levels determined by coupling module 112. In some embodiments, coupling levels below a minimum coupling threshold may be automatically excluded from selection. In some embodiments, coupling levels above a sufficient coupling threshold may be automatically included in the selection. In some embodiments, the minimum coupling threshold may be an absolute value. In some embodiments, the minimum coupling threshold may be dependent on and/or based on one or both of the maximum coupling level and/or an aggregate coupling level based on a subset of values of coupling levels from a corresponding subset of capacitive sensors. In some embodiments, the sufficient coupling threshold may be an absolute value. In some embodiments, the sufficient coupling threshold may be dependent on and/or based on one or both of the maximum coupling level and/or an aggregate coupling level based on a subset of values of coupling levels from a corresponding subset of capacitive sensors.

For example, in some embodiments, selection by selection module 112 may be based on comparisons between the maximum coupling level (e.g. the output signal having the maximum amplitude for either (substantially) the entire sensed information or the maximum energy content for the frequency range corresponding to the coupling information) and the coupling levels for the other (non-maximum) coupling sensors. Comparisons may be based on ratios, variances, and/or other arithmetic and/or statistical manipulations of the coupling levels. For example, the variance of the maximum coupling level may be compared to the variances of one or more other coupling levels to determine selection by selection module 112. The term "substantially the entire sensed information" may be interpreted as the sensed information including all or most of the electrophysiological information and including all or most of the coupling information. In some embodiments, the sensed information may be processed prior to being used as described by selection module 112. For example, signal components having a frequency below a lower frequency threshold may be discarded. The lower frequency threshold may be 20 Hz, 15 Hz, 10 Hz, 5 Hz, 4 Hz, 3 Hz, 2 Hz, 1 Hz, and/or another suitable lower frequency threshold. Such processed sensed information may be referred to as "substantially the entire sensed information."

In some embodiments, selection by selection module 112 may be based on one or more correlation coefficients, e.g. using comparisons thereof. A correlation coefficient may be determined between output signals from two capacitive sensors 143 and/or between the two corresponding coupling levels. Correlation coefficients may include one or more of Pearson's correlation coefficient, rank correlation, and/or other types of statistical correlation. Assuming a maximum capacitive sensor has been determined, a first correlation coefficient may be determined between the corresponding maximum coupling level and the coupling level of a first particular capacitive sensor 143a. A second correlation coefficient may be determined between the maximum coupling level and the coupling level of a second particular capacitive sensor 143b, and so forth for additional coupling levels of other (possibly preliminarily selected on other grounds as described elsewhere herein) capacitive sensors. Selection by selection module 112 may be based on a comparison between the first correlation coefficient, the second correlation coefficient, and so forth. For example, selection module 112 may discard output signals from capacitive sensors having a corresponding correlation coefficient (with the maximum coupling level) below a minimum correlation threshold.

In some embodiments, selection by selection module 112 may be based on a quantification of the amount of information that is included in the output signals of particular capacitive sensors. The amount of information may be determined independently, or relative to the output signals from the maximum sensor. For example, if two capacitive sensors, a first and second capacitive sensor, generated the same or very similar output signals, the additional amount of information added by the second capacitive sensor to the information provided by the first capacitive sensor may be small and/or limited, and may form a basis for excluding the second capacitive sensor from selection by selection module 112.

In some embodiments, selection by selection module 112 may be based on spatial distribution of multiple capacitive sensors 143. Spatial distribution may be used to favor selecting capacitive sensors 143 covering the largest available area of body of engagement 11. In some embodiments, the set of capacitive sensors 143 corresponds to a weighing matrix. Selection by selection module 112 may be implemented by adjusting and/or tuning the weights in the weighing matrix. In some embodiments, spatial distribution may penalize proximity. For example, if a first and second capacitive sensor have similar coupling levels according to some determination (for example in comparison to the maximum capacitive sensor), by virtue of taking spatial distribution into account, the first capacitive sensor may be favored over the second capacitive sensor because it is furthest away from the maximum capacitive sensor. Conversely, the second capacitive sensor may be penalized (e.g. by reducing its weight factor in the weighing matrix) because it is closest to the maximum capacitive sensor. In some embodiments, spatial distribution may only be used responsive to at least a minimum number of capacitive sensors 143 having at least a minimum coupling level, and/or responsive to other conditions.

Selection module 112 may be configured to determine multiple selections, for example including a first selection, a second selection, and so forth. Multiple selections may be determined and/or performed in sequence and/or simultaneously. Selections may act as a filter on which capacitive sensors are deemed to have produced reliable and/or useful information. For example, the first selection may be based on the amplitude of the coupling levels of a set of capacitive sensors 143 (as described elsewhere), thus establishing a first subset of capacitive sensors 143 and discarding sensed information from capacitive sensors outside of the first subset. Selection for such a subset may be referred to as "meeting" or "passing" the selection. A second selection may be based on comparisons of correlation coefficients between the maximum coupling level and the coupling levels of capacitive sensors in the first subset. Based on the second selection, a second subset is determined that forms a subset of the first subset, thud discarding sensed information from capacitive sensors 143 outside of the second subset. Selection module 112 is not limited to a first and second selection, but rather may be configured to perform a set of two, three, or more selections, which may be applied subsequently, to iteratively discard individual capacitive sensors (and their corresponding sensed information) until a final subset of selected capacitive sensors has been determined, including only those capacitive sensors that meet and/or pass all performed selections.

Reconstruction module 113 of system 10 in FIG. 3 is configured to determine an electrocardiogram (ECG) signal. Determinations by reconstruction module 113 may be based on output signals generated by one or more capacitive sensors 143. In some embodiments, determinations by reconstruction module 113 may be based on output signals by a subset of selected capacitive sensors, e.g. as selected by selection module 112. Operation of reconstruction module 113 may be based on techniques described in U.S. Pat. No. 8,332,021, filed Jan. 20, 2010 by Vullings et al., titled "Fetal Monitoring." Alternatively, and/or simultaneously, operation of reconstruction module 112 may be based on blind source separation methods, template matching approaches, and/or other techniques that can be used for electrocardiogram (ECG) reconstruction, such as techniques based on using the emitted carrier signal. Exemplary operations performed by reconstruction module 113 may include one or more of the following: applying a low-pass filter to, at least, remove one or more (about) 50 Hz to (about) 60 Hz noise signals caused by ambient electrical devices, determine a vectorcardiogram (VCG, illustrated in FIG. 4A) based on output signals from selected capacitive sensors, approximating the vectorcardiogram (VCG) for several overlaid heartbeats (see FIG. 4A) by an ellipse and projecting the vectorcardiogram (VCG) onto the long axis of the ellipse, or alternatively, performing another projection suitable for maximal R-peak detection on the reconstructed electrocardiogram (ECG) signal that results from the projection.

Additional steps in the operation of reconstruction module 113 may include performing R-peak detection on the reconstructed signal, applying Kalman filtering using the detected R-peaks, and/or re-calculating a vectorcardiogram (VCG) signal from the Kalman-filtered signal and projecting that VCG signal to the standard Einthoven leads, as may be commonly used in standard ECG analysis. Kalman filtering may be implemented by maximizing the Bayesian evidence function of a sequential ECG estimation and by exploiting the spatial correlation between several simultaneously recorded ECG signals, respectively. The noise covariance estimation thus obtained may be used in Kalman filtering to either assign and/or ascribe more weight to the most recently obtained sensed information if this sensed information contains morphological variability, or to assign and/or ascribe less weight in cases of no or insignificant morphological variability.

Figure 4A:
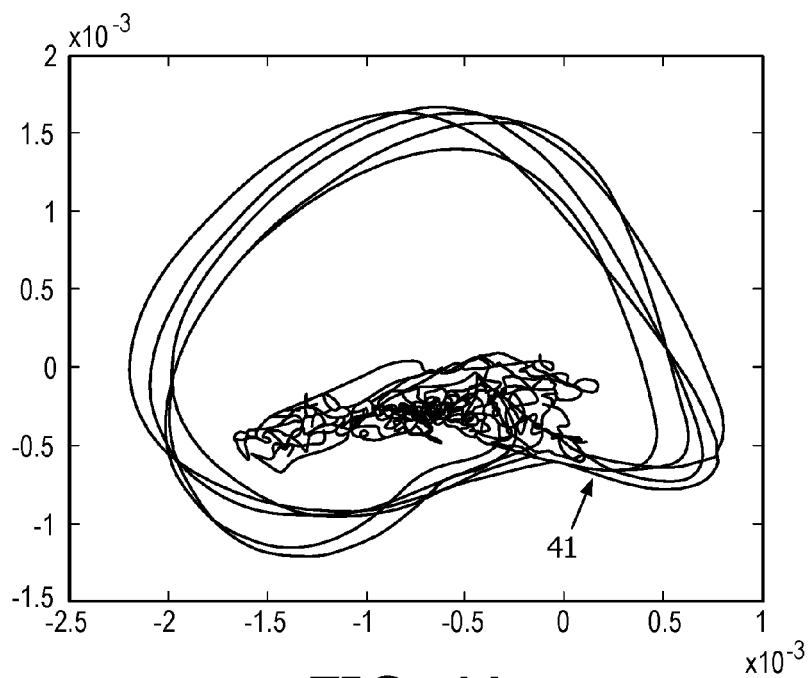
FIGS. 4A-4B-4C illustrate graphs of measurements made in accordance with one or more embodiments.
Figure 4B:
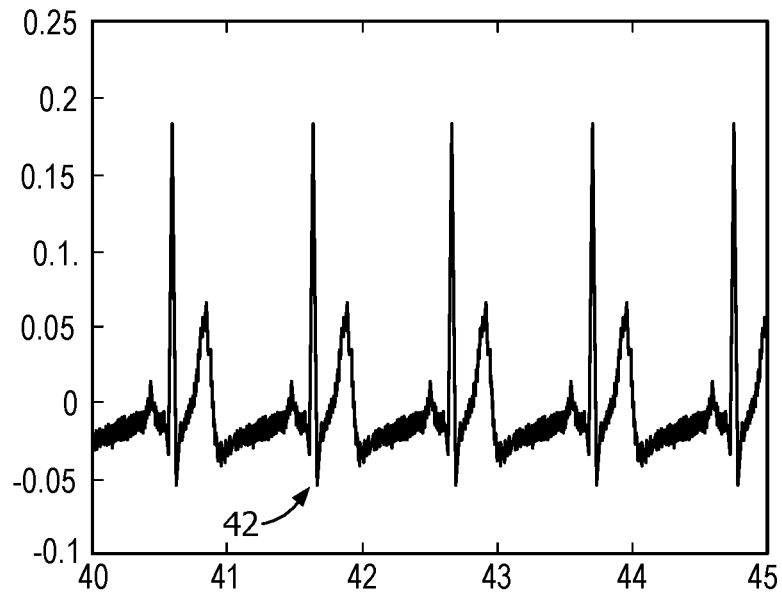
Figure 4C:
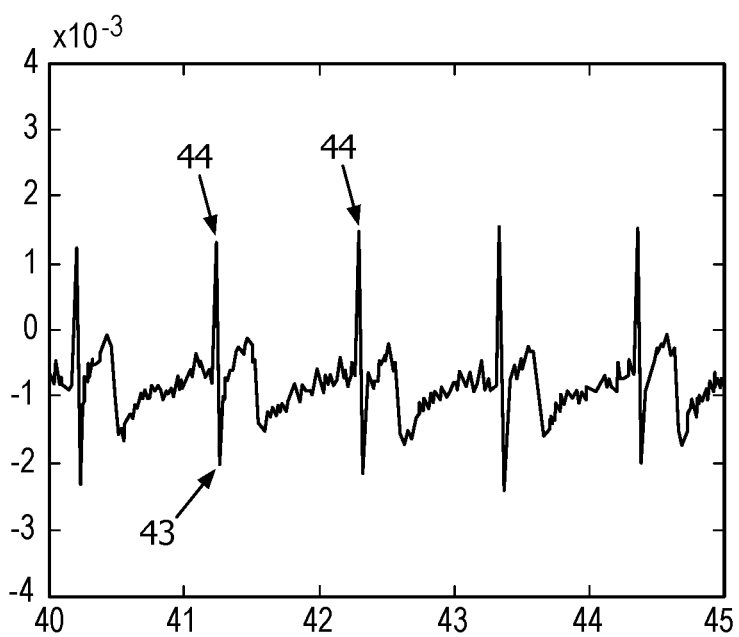

By way of illustration, FIG. 4B illustrates a reference ECG signal 42, depicting several heartbeats, as may be generated through commonly used techniques. The X-axis depicts time; the Y-axis depicts amplitude in Volts. FIG. 4A illustrates a determined vectorcardiogram (VCG) signal 41 based on output signals from 7 capacitive sensors, measured during testing. The X and Y-axis represent distance in the plane in which the capacitive sensors are placed. Several overlaid heartbeats are depicted in FIG. 4A. FIG. 4C illustrates the reconstructed ECG signal 43 based on the determined VCG signal 41 from FIG. 4A. Reconstructed ECG signal 43 corresponds closely to reference ECG signal 42. R-peaks 44 are clearly detected and/or depicted in reconstructed ECG signal 43.

Figure 5:
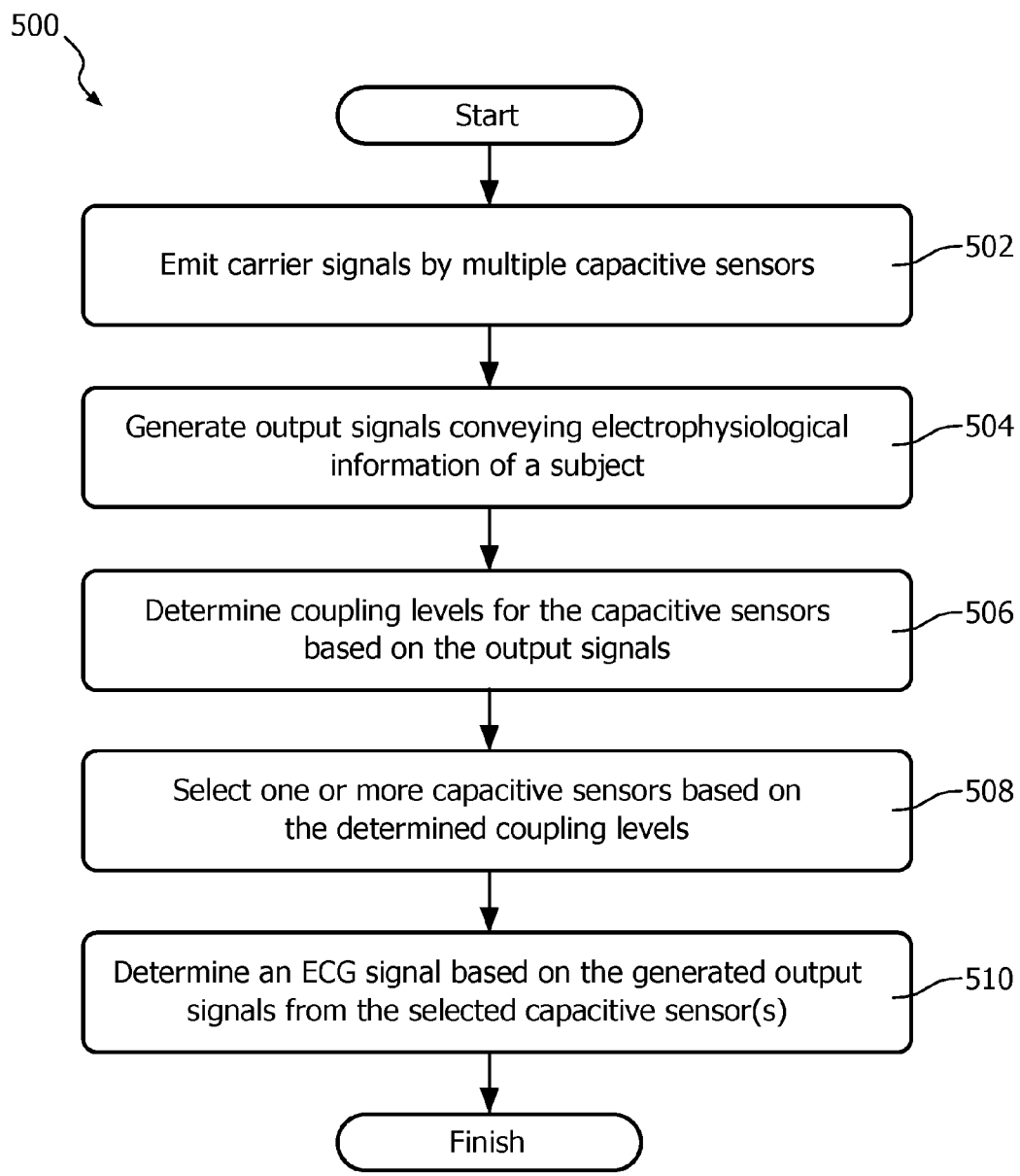
FIG. 5 illustrates a method for determination of one or more ECG signals of a subject, in accordance with one or more embodiments.

FIG. 5 illustrates a method 500 of providing electrocardiography (ECG) monitoring of subject 106. The operations of method 500 presented below are intended to be illustrative. In certain embodiments, method 500 may be accomplished with one or more additional operations not described, and/or without one or more of the operations discussed. Additionally, the order in which the operations of method 500 are illustrated in FIG. 5 and described below is not intended to be limiting.

In certain embodiments, method 500 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, carrier signals are emitted by multiple capacitive sensors, in proximity of a subject. In some embodiments, operation 502 is performed by a capacitive sensors the same as or similar to capacitive sensors 143 (shown in FIGS. 1 and 2 and described herein).

At an operation 504, output signals are generated, conveying electrophysiological information of a subject. The output signals include a representation of the emitted carrier signals. In some embodiments, operation 504 is performed by capacitive sensors the same as or similar to capacitive sensors 143 (shown in FIGS. 1 and 2 and described herein).

At an operation 506, coupling levels are determined for individual ones of the capacitive sensors based on the generated output signals. In some embodiments, operation 506 is performed by a coupling module the same as or similar to coupling module 111 (shown in FIG. 3 and described herein).

At an operation 508, one or more capacitive sensors are selected based on the determined coupling levels. In some embodiments, operation 508 is performed by a selection module the same as or similar to selection module 112 (shown in FIG. 3 and described herein).

At an operation 510, an electrocardiogram (ECG) signal is determined based on the generated output signals from the selected one or more capacitive sensors. In some embodiments, operation 510 is performed by a reconstruction module the same as or similar to reconstruction module 113 (shown in FIG. 3 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system for electrocardiography (ECG) monitoring of a subject, the system comprising:
 multiple non-invasive capacitive sensors configured to generate output signals conveying electrophysiological information of the subject, wherein the multiple capacitive sensors include at least three non-invasive capacitive sensors that are free from attachment to the subject, wherein the non-invasive capacitive sensors are further configured to emit carrier signals, and wherein the generated output signals of an individual one of the non-invasive capacitive sensors are electrophysiological signals of the subject, the physiological signals including a representation of the carrier signals;
computer program modules; and
one or more processors configured to execute the computer program modules, the computer program modules comprising:
a coupling module configured to determine coupling levels for individual ones of the non-invasive capacitive sensors based on the generated output signals
a selection module configured to select one or more capacitive sensors based on the determined coupling levels; and
a reconstruction module configured to determine an electrocardiogram (ECG) signal based on the generated output signals from the selected one or more capacitive sensors;
wherein the coupling module is further configured to determine which capacitive sensor has the highest coupling level, and wherein selection of the one or more capacitive sensors is based on one or more correlation coefficients between the output signals generated by the capacitive sensor having the highest coupling level and the output signals generated by one or more other capacitive sensors, the correlation coefficient including at least one of a Pearson's correlation coefficient and a rank correlation coefficient.

2. The system of claim 1, wherein the coupling module is further configured to determine which capacitive sensor has the highest coupling level.

3. The system of claim 1, wherein selection of the one or more capacitive sensors is further based on spatial distribution of the one or more capacitive sensors.

4. The system of claim 1, wherein the reconstruction module is configured to determine the electrocardiogram signal by determining a vectorcardiogram (VCG) signal based on the generated output signals from the selected one or more capacitive sensors, approximating the vectorcardiogram signal by an ellipse having a long axis, and projecting the vectorcardiogram signal onto the long axis of the ellipse.

5. The system of claim 1, wherein the multiple non-invasive capacitive sensors are configured to generate the output signals non-invasively and motion-tolerant to limited motion of a subject.

6. A method of providing electrocardiography (ECG) monitoring of a subject, the method comprising:
emitting, by multiple non-invasive capacitive sensors that are not in physical contact with the patient, carrier signals, wherein the multiple capacitive sensors include at least three non-invasive capacitive sensors;
generating, by the multiple capacitive sensors, output signals conveying electrophysiological information of the subject, wherein the output signals of an individual one of the non-invasive capacitive sensors are electrophysiological signals of the subject, the physiological signals including a representation of the carrier signals;
determining coupling levels for individual ones of the capacitive sensors based on the generated output signals including determining which capacitive sensor has the highest coupling level;
selecting one or more capacitive sensors based on the determined coupling levels based on one or more correlation coefficients between the output signals generated by the capacitive sensor having the highest coupling level and the output signals generated by one or more other capacitive sensors; and
determining an electrocardiogram (ECG) signal based on the generated output signals from the selected one or more capacitive sensors;
wherein the step of selecting one or more capacitive sensors is based on one or more correlation coefficients between the output signals generated by the capacitive sensor having the highest coupling level and the output signals generated by one or more other capacitive sensors, the correlation coefficient including at least one of a Pearson's correlation coefficient and a rank correlation coefficient.

7. The method of claim 6, wherein selection of the one or more capacitive sensors is further based on spatial distribution of the one or more capacitive sensors.

8. The method of claim 6, wherein determining the electrocardiogram (ECG) signal includes:
determining a vectorcardiogram (VCG) signal based on the generated output signals from the selected one or more capacitive sensors;
approximating the vectorcardiogram signal by an ellipse having a long axis; and
projecting the vectorcardiogram signal onto the long axis of the ellipse.

9. The method of claim 6, wherein the multiple non-invasive capacitive sensors are configured to generate the output signals non-invasively and motion-tolerant to limited motion of a subject.

10. The method of claim 6, wherein the multiple non-invasive capacitive sensors are free from attachment to the subject.

11. A system configured to provide electrocardiography (ECG) monitoring of a subject, the system comprising:
means for emitting carrier signals including multiple elements configured to emit carrier signals, wherein the multiple elements include at least three non-invasive elements;
means for generating output signals conveying electrophysiological information of the subject, wherein the output signals of an individual element include a representation of the carrier signals emitted by the individual element, wherein the means for generating output signals is non-invasive to the subject;
means for determining coupling levels for the means for emitting carrier signals based on the generated output signals;
means for selecting one or more elements of the means for emitting carrier signals based on the determined coupling levels; and
means for determining an electrocardiogram (ECG) signal based on the generated output signals from the selected elements selected by the means for selecting;
wherein the means for determining coupling levels is configured to determine which non-invasive element has the highest coupling level, and wherein the selection means for selecting is based on one or more correlation coefficients between the output signals generated by the non-invasive element having the highest coupling level and the output signals generated by one or more other non-invasive element, the correlation coefficient including at least one of a Pearson's correlation coefficient and a rank correlation coefficient.

12. The system of claim 11, wherein operation of the means for selecting is further based on spatial distribution of the one or more elements of the means for emitting carrier signals.

13. The system of claim 11, wherein the means for determining the electrocardiogram (ECG) signal includes:

means for determining a vectorcardiogram signal based on the generated output signals from the selected one or more capacitive sensors;
means for approximating the vectorcardiogram signal by an ellipse having a long axis; and
means for projecting the vectorcardiogram signal onto the long axis of the ellipse.

14. The system of claim 11, wherein the means for generating the output signal are configured to generate the output signals non-invasively and motion-tolerant to limited motion of a subject.

15. The system of claim 11, wherein the means for emitting the carrier signals and the means for generating the output signals comprise at least three multiple non-invasive capacitive sensors.

16. The system of claim 15, wherein the at least three multiple non-invasive capacitive sensors are free from attachment to the subject.

17. The system of claim 11, wherein the means for determining coupling levels, the means for selecting one or more elements of the means for emitting carrier signals, and the means for determining the ECG signal each comprise at least one electronic processor.

* * * * *